United States Patent [19]

Mummert

[11] 4,364,128

[45] Dec. 21, 1982

[54] ARTIFICIAL FOOT

[75] Inventor: Thomas A. Mummert, Toledo, Ohio

[73] Assignee: Jobst Institute, Inc., Toledo, Ohio

[21] Appl. No.: 297,996

[22] Filed: Aug. 31, 1981

[51] Int. Cl.³ .............................................. A61F 1/08
[52] U.S. Cl. ........................................... 3/6.1; 3/21; 3/32; 3/33
[58] Field of Search ........................................ 3/6-7, 3/21, 23, 30-35

[56] References Cited

U.S. PATENT DOCUMENTS

| | | | |
|---|---|---|---|
| 1,289,580 | 12/1918 | Vincenti | 3/36 |
| 2,036,830 | 4/1936 | Rowley | 3/6.1 |
| 2,470,480 | 5/1949 | Fogg | 3/6.1 X |
| 2,475,372 | 7/1949 | Catranis | 3/6.1 X |
| 2,687,533 | 8/1954 | McCormick | 3/32 |
| 2,731,645 | 1/1956 | Woodall | 3/6 |
| 3,551,914 | 1/1971 | Woodall | 3/6 |
| 3,800,334 | 4/1974 | Friberg | 3/23 |

Primary Examiner—Ronald L. Frinks
Attorney, Agent, or Firm—Wilson, Fraser, Barker & Clemens

[57] ABSTRACT

An artificial foot for attachment to a prosthetic device securable to a leg stump. The artificial foot is adjustable in length and in height of the instep so as to permit the foot to be snugly inserted in a conventional shoe. The artificial foot includes a simulated toe portion which is horizontally pivotally connected to a sole plate. A spring-pressed linkage normally maintains the simulated toe portion in an aligned position with the sole plate, but permits upward pivotal movement of the toe portion in response to the forces encountered in taking a step. A latching lever frictionally engages the spring-pressed linkage to latch the pivoted toe portion in its upward position during that portion of the step wherein the weight is carried by the other foot. The artificial foot is connected to the bottom plate of a prosthetic device by a plurality of cushion plugs. The rearmost one of the cushion plugs mounts a depending plunger which is operatively connected with the latching lever to release same when the heel portion of the artificial foot first engages the ground at the end of a step, thereby permitting the simulated toe portion to resume its aligned position.

13 Claims, 3 Drawing Figures

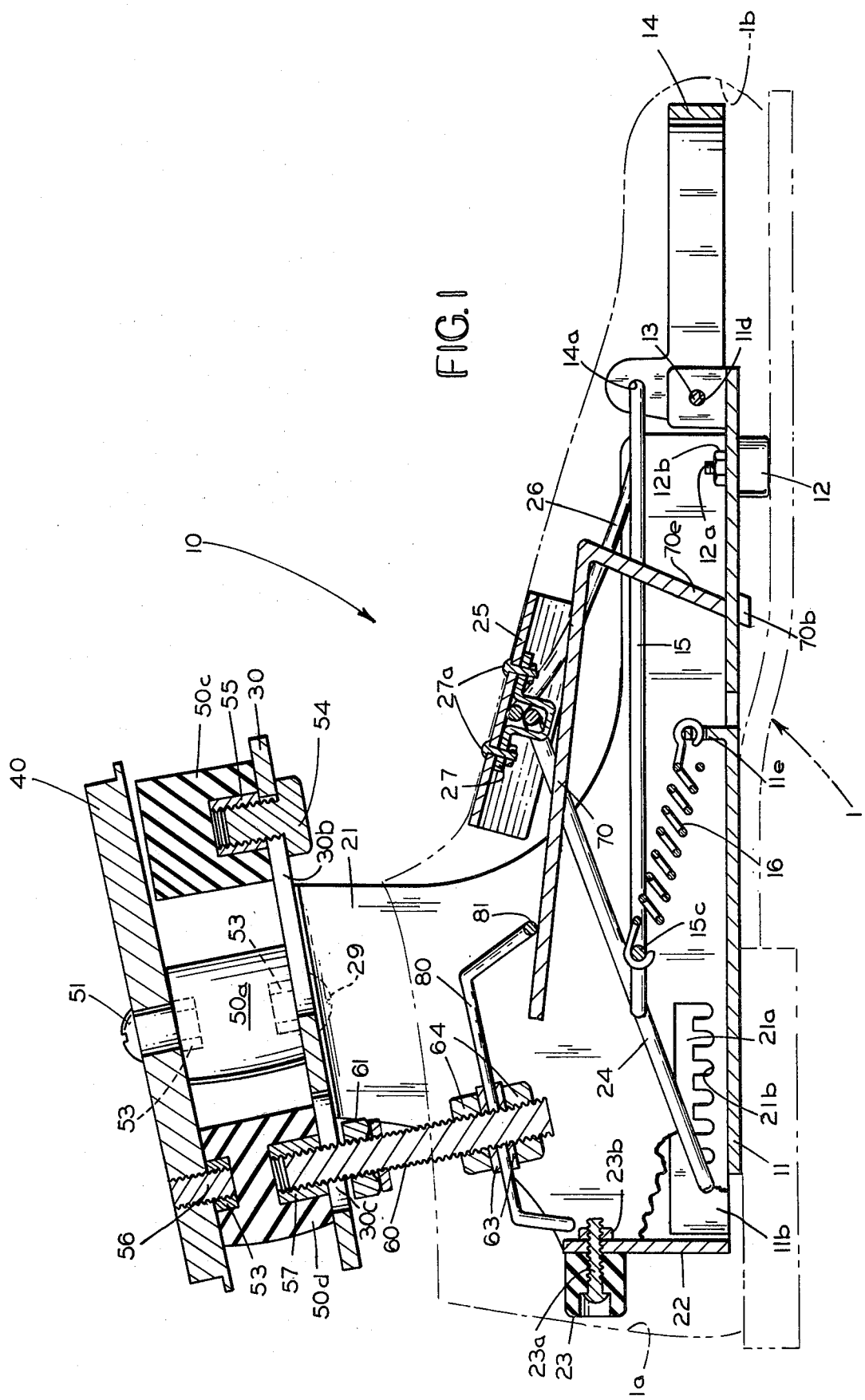

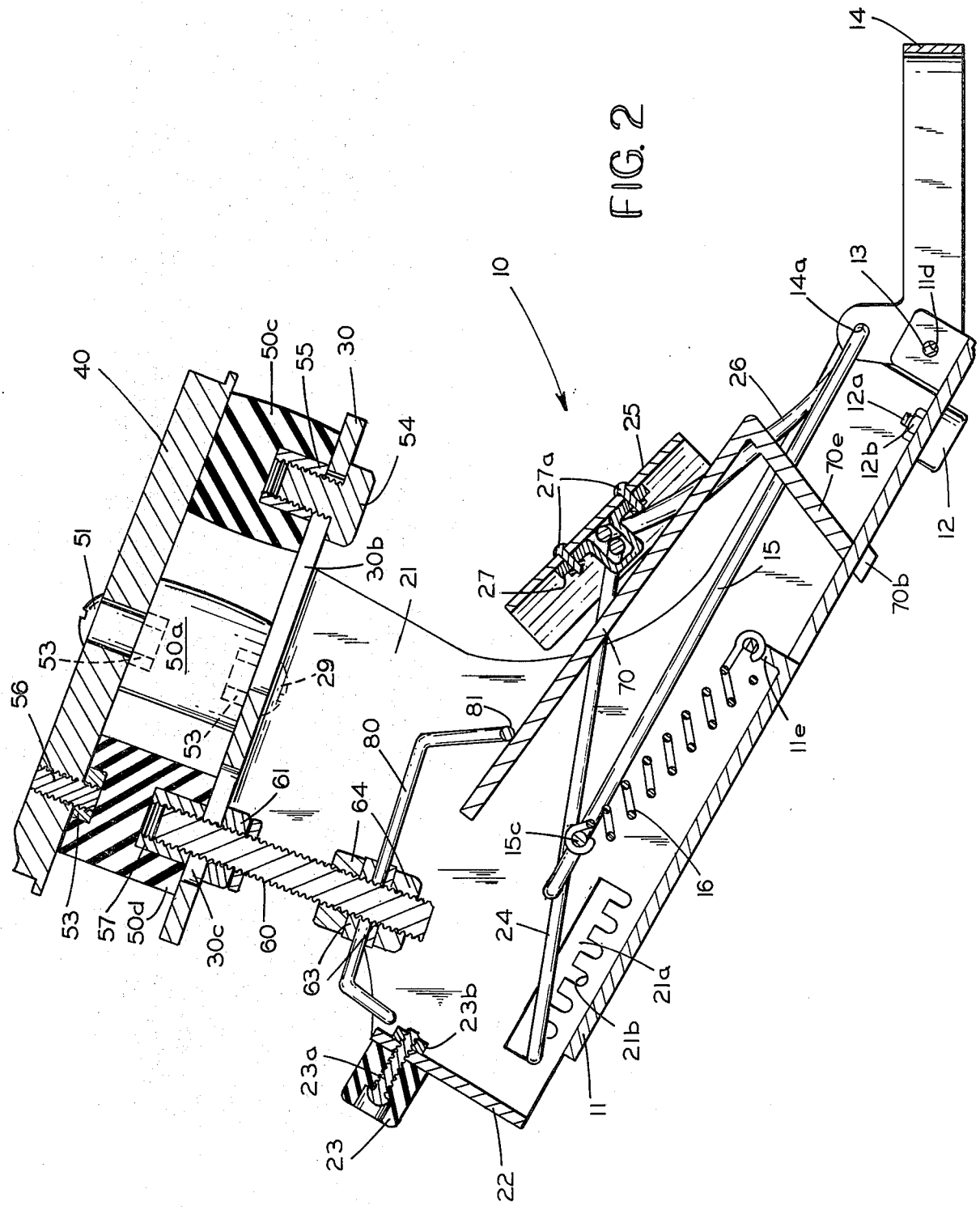

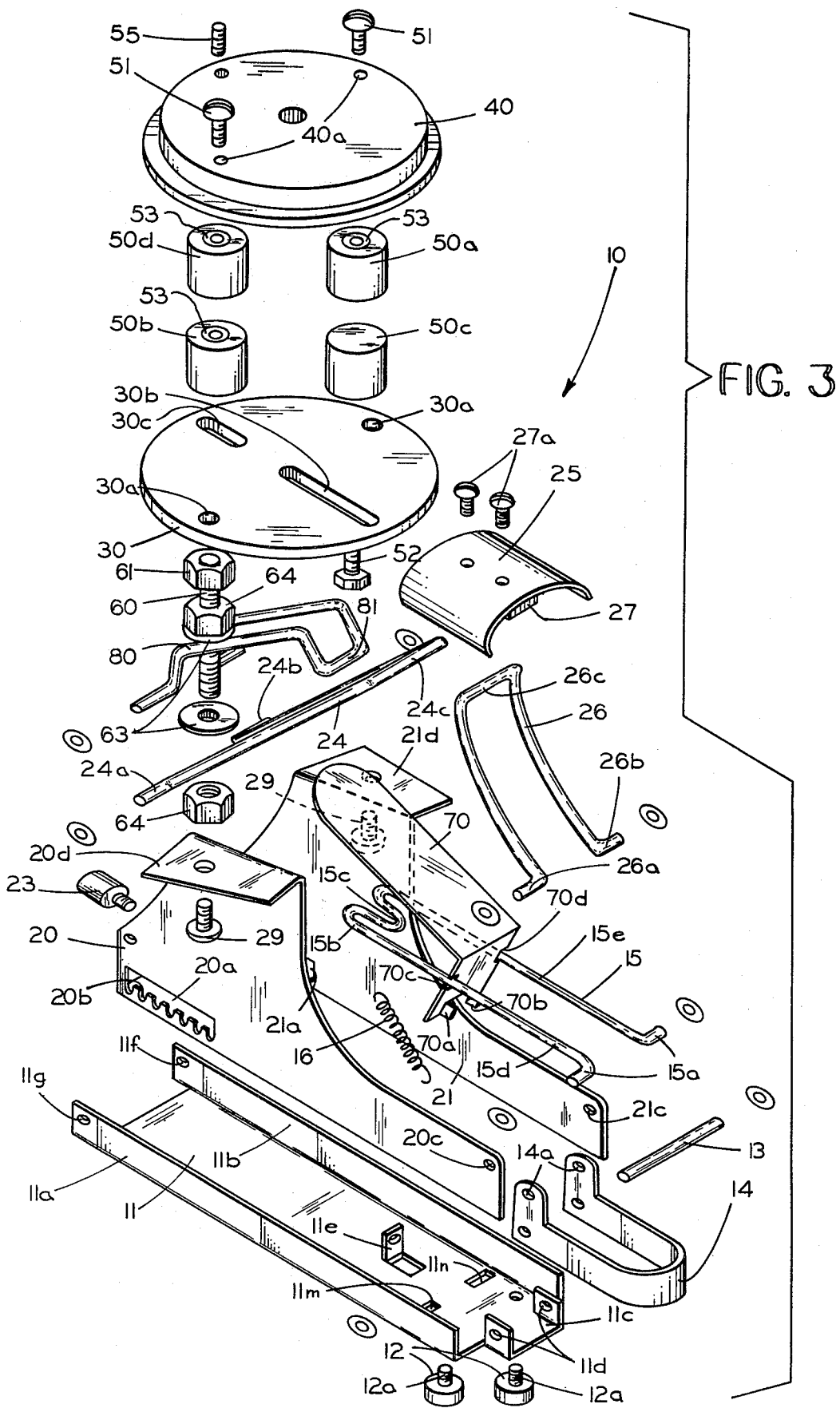

ARTIFICIAL FOOT

FIELD OF THE INVENTION

This invention relates to an artificial foot for attachment to a prosthetic device securable to a leg stump, and particularly to an artificial foot which can be temporarily employed following surgery and which accomodates the mounting thereon of the patient's normal shoe.

HISTORY OF THE PRIOR ART

There are literally hundreds of prior patents dealing with artificial feet for patients who suffer the severance of portion of a leg. While there are many prior art prosthetic devices attachable to the leg stump which are satisfactory for permanent use by a patient once his recovery has been established, such devices require custom manufacture and fitting which involves a substantial delay in making the patient ambulatory. There is a distinct need for an economical artificial foot which may be inserted into the patient's regular shoe, but at the same time provide the required flexibility of movements normally associated with walking so that when attached to the limb stump by a prosthetic device, the patient may become ambulatory at a much earlier stage in his recovery. The psychological value of letting the amputee relearn to walk in his own shoes cannot be over estimated.

Such artificial foot must necessarily incorporate a cushion connection to the prosthetic device and also permit the normal upward flexure of the toe portion of the artificial foot that is encountered when walking naturally. Moreover, it is most important that the toe portion of the artificial foot be latched in its upwardly pivoted relationship to the remainder of the foot during that portion of the step wherein the patient's weight is carried by the other leg, to prevent the toe of the shoe from dragging along the ground, which would necessitate the patient adopting a limp in order to overcome such dragging motion. Additionally, as the heel of the shoe containing the artificial foot strikes the ground at the end of a step, it is desirable that the simulated toe portion of the artificial foot be automatically moved downwardly to its horizontally aligned position with respect to the sole portion of the artificial foot so that the shoe containing the artificial foot is in flat engagement with the ground when the entire weight of the patient is supported by the amputated leg.

If the patient's normal shoe is to be employed in conjunction with the aritifical foot, it necessarily follows that the artificial foot must incorporate some means for adjusting the effective length of the artificial foot and also the height of the instep surface of the artificial foot in order to permit the patient's shoe to be securely and neatly fastened to the artificial foot.

Although the voluminous prior art incorporates disclosures of artificial feet having a simulated toe portion pivoted to a sole portion, the automatic control of the position of such toe portion through utilization of forces normally imparted to the artificial foot during walking, has not been disclosed in the prior art.

SUMMARY OF THE INVENTION

This invention provides an artificial foot adapted to be inserted in the amputee's normal shoe and to be adjustable to snugly fit the salient interior portions of such shoe, such as the end of the toe, the heel and the instep.

A sole plate is provided having means at the front end thereof for horizontally pivotally mounting a member simulating the toes of the foot. A control linkage is provided, including a stretched spring, for urging the toe simulating portion of the device to its normal position of horizontal alignment with the sole portion of the artificial foot. A pair of upstanding side plates are provided which are integrally connected by a transverse heel portion. An elastomeric bumper is secured to the transverse heel portion to bear against the internal surface of the heel portion of the shoe. To provide a snug fitting of the artificial foot in the patient's normal shoe, the side plate elements are longitudinally adjustably mounted to the sole plate so as to lengthen or shorten the distance of the heel bumper to either the simulated toe portion or to a simulated ball element provided on the bottom of the sole plate to conform to the interior longitudinal dimension of the patient's shoe.

The top walls of the side plates are bent outwardly and rigidly secured to a circular leg force receiving plate. Such plate is in turn connected by a plurality of elastomeric plugs to a disc shaped plate forming the bottom element of a prosthetic device engagable with the limb stump. At least four equally peripherally spaced elastomeric plugs are provided, so as to permit cushioned pivotal movement between the prosthetic plate and the leg force receiving plate about a plurality of horizontal axes. Two of the aforementioned elastomeric plugs are disposed in longitudinal alignment with the longitudinal center axis of the artificial foot and the other two are transversely disposed. The rearmost plug is most compressed during that portion of a step wherein the heel of the shoe containing the artificial foot first strikes the ground. The degree of compression of the rearmost plug is gradually reduced and is transferred to the forward plug as the toe portion of the shoe containing the artificial foot is pivoted relative to the sole of the foot to accomodate the raising of the heel portion from the ground. A depending plunger is attached to the rearmost plug and is downwardly shiftable by the compression of such plug due to the leg forces applied thereto by the prosthetic plate.

A latch is provided comprising a pivoted lever having a slotted frictional engagement with the control linkage which imparts a pivotal bias to the toe portion of the artificial foot. The nonpivoted end of the lever is disposed in the path of the depending plunger and is pivoted thereby to a position releasing the frictional drag of the lever slots on the control linkage, thus permitting the toe simulating portion of the artificial foot to return to its horizontally aligned position as the heel of the shoe containing the artificial foot strikes the ground at the end of a step. The toe simulating portion is, however, free to pivot upwardly relative to the sole portion against the bias of the retaining spring as the artificial foot is rocked forward to elevate the heel during the next phase of the step. As the heel is elevated, the compressive forces on the rearmost plug are released, and the depending plunger is withdrawn from engagement with the friction lever, which then assumes a binding position with respect to the simulated toe control linkage and holds the simulated toe in its upwardly pivoted position until the completion of the next step with the amputated limb.

Further objects and advantages of the invention will be readily apparent to those skilled in the art from the following detailed description, taken in conjunction with the annexed sheets of drawings, on which is shown a preferred embodiment of the invention.

BRIEF DESCRIPTION OF DRAWINGS

FIG. 1 is a vertical sectional view of an artificial foot embodying this invention with the elements thereof shown in the positions occupied as the heel of the shoe containing the artificial foot first strikes the ground.

FIG. 2 is a view similar to FIG. 1 but showing the elements of the artificial foot in the positions occupied when the heel portion of the shoe containing the artificial foot has left the ground at the initiation of a step by the amputated limb.

FIG. 3 is an exploded perspective view of the artificial foot illustrated in FIGS. 1 and 2.

DESCRIPTION OF THE PREFERRED EMBODIMENT

Referring to the drawings, the numeral 10 indicates an artificial foot assembly constructed in accordance with this invention and illustrated in FIGS. 1 and 2 in an inserted relationship to a conventional shoe 1 which, for psychological reasons, is preferably one of the patient's shoes for the foot that has been removed by amputation.

As best shown in the exploded view of FIG. 3, the artificial foot assembly 10 comprises a channel shaped sole plate 11 having transversely spaced upstanding wall portions 11a and 11b. The dimensions of sole plate 11 are such that is may be freely inserted to lie in the bottom portions of the shoe 1. If desired, a pair of depending cushion elements 12 may be secured to the forward portions of sole plate 11 by bolts 12a and nuts 12b at the location corresponding to the ball of a natural foot.

The extreme forward end of sole plate 11 is of reduced lateral extent, as indicated at 11c, and is provided at its lateral extremities with upstanding lugs 11d. Such lugs are apertured to receive a pivot mounting pin 13 for effecting the horizontal pivotal mounting of a generally U-shaped toe simulator element 14. Toe simulator element 14 extends into those portions of the shoe 1 normally occupied by the toes.

At the rear end of toe simulator 14, a pair of upstanding ears 14a are provided, which respectively receive the laterally bent ends 15a of a U-shaped control linkage element 15. Element 15 extends rearwardly in generally parallel relationship with the sole plate 11 and is urged forwardly by a tension spring 16. One end of spring 16 is secured to a re-entrant portion 15c formed in the bight portion 15b of the control link 15 and the other end of spring 16 is secured to an upstanding flange 11e punched from the sole plate 11. It is therefore apparent that the toe simulator 14 is resiliently urged to a position of horizontal alignment with the sole plate 11 or, in other words, to the position simulating the configuration of the foot when the amputated leg is at rest in a standing position, as specifically illustrated in FIG. 1. The toe simulator 14 is, however, free to pivot upwardly relative to the sole plate 11 and hence assumes the position illustrated in FIG. 2, which corresponds to the position of a normal foot when the heel is elevated as a consequence of taking a forward step by the other leg.

The artificial foot assembly 10 further includes a pair of upstanding, laterally spaced, ankle simulating plates 20 and 21. The bottom edges of ankle plates 20 and 21 respectively rest on the sole plate 11 adjacent to the sole plate side walls 11a and 11b respectively. Ankle plates 20 and 21 are integrally connected by a transverse heel plate 22 which mounts an appropriate resilient heel cushion 23 by a bolt 23a and cooperating nut 23b.

To provide a snug fit of the artificial foot 10 within the patient's normal shoe 1, adjustment of the effective length of the artificial foot is provided by a pair of longitudinally extending slots 20a and 21a respectively provided in the ankle plates 20 and 21 adjacent the rear ends thereof and lying in close proximity to the sole plate 11. Slots 20a and 21a are respectively provided with a plurality of vertical recesses 20b and 21b in the lower slot surfaces. Such recesses may be successively aligned with transversely aligned holes 11f and 11g respectively provided in rearward extension of the sole plate side walls 11a and 11b by moving the ankle plates 20 and 21 longitudinally relative to sole plate 11. The effective length of the artificial foot 10 may then be adjusted by passing a retaining pin through the sole plate side wall holes 11f and 11g and through any selected aligned pair of recesses 20b and 21b provided in the ankle plates 20 and 21.

Instead of using a transverse pin to effect such adjustment of the length of the artificial foot 10, this invention provides a generally U-shaped rod 24 having outturned lateral extremities 24a and 24b which respectively engage the sole plate holes 11f and 11g and a selected aligned pair of ankle plate recesses 20b and 21b. The length adjustment can then be accomplished without removing the rod extremities from the side plate holes by pivoting sole plate 11 to move the rod extremities 24a and 24b into the upper part of slots 20a and 21a, then sliding the sole plate 11 relative to ankle plates 20 and 21.

The bight portion 24c of the U-shaped rod 24 is then employed to support a transversely curved plate 25 which simulates the top surface of the instep portion of the foot, i.e., that portion of the foot overwhich the laces of a shoe are normally located. The instep plate 25 is additionally supported in overlying relationship to the sole plate 11 by a second U-shaped support loop 26 which has outturned lateral extremities 26a and 26b respectively mounted in aligned holes 20c and 21c respectively provided in the forward ends of ankle plates 20 and 21. The bight portions 24c and 26c of the support loops 24 and 26 are respectively pivotally secured to the underside of the instep plate 25 by a U-shaped clamp element 27, which in turn is secured to the instep plate 25 by a pair of bolts 27a.

With the described construction, it will be apparent that the vertical position of the instep plate 25 will be shifted vertically in direct proportion to the selected length of the artificial foot 10. As the support rod 24 is moved forwardly along the ankle plate recesses 20b and 21b, which corresponds to effectively lengthening the artificial foot 10, the instep plate 25 will be elevated relative to the sole plate 11. The tight lacing of the shoe 1 over instep plate 25 snugly secures shoe 1 to the artificial foot 10. Thus, the construction of this invention provides an automatic contouring of the artificial foot 10 to snugly conform to the patient's shoe over a normal range of sizes for a man. Smaller overall designs would be required to accomodate womens or childrens shoes.

The top portion of each ankle plate 20 and 21 is provided with a laterally outturned flange 20d and 21d respectively. Such flanges are rigidly secured to a disc shaped plate 30 by bolts 29. Plate 30, which hereinafter will be referred to as the leg force receiving plate, is in turn secured to a prosthesis plate 40 which forms the bottom element of a prosthetic device (not shown) which is conventionally secured to the remaining limb of the patient. Such prosthetic device may comprise any one of a number of such devices that are currently manufactured and sold. It will be understood, however, that the prosthetic device effects a rigid securement to the remaining limb portion of the patient so that the prosthetic bottom plate 40 moves with such limb stump, particularly when the limb stump is moved in the normal process of walking.

The connection of the leg force receiving plate 30 to the prosthetic bottom plate 40 is effected in such manner as to permit limited, cushioned pivotal movement between such plates. Preferably, at least four quadrilaterally spaced elastomeric plug or cushion elements 50, 50b, 50c and 50d are provided intermediate the plates 30 and 40. Two of such elastomeric cushions, 50a and 50b, are mounted in laterally aligned relationship between the plate 30 and 40 by screws 51 and 29 which respectively traverse appropriate holes 40a provided in the prosthetic bottom plate 40 and holes 30a provided in the leg force transmitting plate 30 and engage internally threaded inserts 53 in cushions 50a and 50b.

The remaining two elastomeric plugs or cushions 50c and 50d are longitudinally aligned with the longitudinal central axis of the artificial shoe 10. The forward cushion 50c is secured only to the leg force receiving plate 30 by a bolt 54 which traverses a radially disposed slot 30b provided in the plate 30 and engages an internally threaded insert 55 in cushion 50c. Cushion 50c has only abutting contact with the undersurface of the prosthetic bottom plate 40. The provision of the radial slot 30b permits the radial position of the forward cushion plug 50c to be selectively adjusted to provide the desired amount of compression which of course is a factor of the weight of the patient and the desired stride. For a heavier patient, the position of the forward cushion plug is moved forwardly in the slot 30b.

The rearmost cushion plug 50d is secured in depending relationship to the prosthetic plate 40 by a bolt 56 which threadably engages an internally threaded insert 53 integrally molded in the top of plug 50d. An internally threaded sleeve 57 is integrally molded in the lower portion of the rearmost plug 50d and receives the top end of a threaded plunger 60 which projects downwardly thru a radial slot 30c in plate 30 and then between the ankle plates 20 and 21 for purpose to be hereinafter described. It will be noted that the plunger 60 moves in a vertically inclined path as the artificial foot 10 is moved through a step. Thus, as the artificial foot 10 is moved to the position where the heel of the shoe 1 initially strikes the ground or other walking surface, a maximum compressive force is imposed on the rear cushion plug 50d and this results in a downward shifting of the plunger 60. In the middle of the step, when the weight is equally distributed along the sole plate 11, the degree of compression imposed on the rearmost cushion plug 50d is reduced and the depending plunger 60 moves upwardly. At the end of the step, adjustable lock nuts 61 on plunger 60 engages the plate 30 to elevate the heel portion of the artificial foot 10.

In accordance with this invention, this shifting movement of the depending plunger 60, which is a function of the relative pivotal movement of the prosthetic bottom plate 40 with respect to the leg force receiving plate 30 about a transverse horizontal axis, is employed to effect the automatic latching and releasing of the toe simulator 14 in the elevated position relative to the sole plate 11 in the proper sequence in the movement of the artifical foot through a normal step. A friction type latch lever 70 is provided which is of generally angular configuration and has one end thereof pivotally mounted to the sole plate 11 for movement in a vertical plane by virtue of having integral projections 70a and 70b enter rectangularly shaped apertures 11m and 11n provided in the sole plate 11 and engage the bottom of sole plate 11 to support lever 70 in cantilever fashion. One portion 70e of the lever 70 extends upwardly between the arms 15d and 15e of the Ushaped control linkage 15 and is provided with slots 70c and 70d which respectively engage the arm portions 15d and 15e. The clearance between the slots 70c and 70d and the arm portions 15d and 15e of control rod 15 is limited by the relative angle between lever 70 and such arm portions so that the frictional engagement normally tends to pivot the lever 70 in a clockwise direction and effect a binding of such lever on the control rod arms 15d and 15e to prevent the movement of the toe simulator 14 from its position shown in FIG. 2 to the position shown in FIG. 1. However, a counterclockwise rotation of the latching lever 70 will release the frictional engagement of the lever slots 70c and 70d with the arms 15d and 15e of the control rod 15 and permit the control rod 15 to slide freely forwardly to permit the toe simulator 14 to assume the position shown in FIG. 1. Additionally, upward pivotal movement of toe simulator 14 is not prevented by the frictional drag of latching lever 70 on control rod 15.

The aforedescribed downward movement of the depending plunger 60 is utilized to effect the counterclockwise pivoting of the latching lever 70 to its control rod releasing position. Plunger 60 has a generally U-shaped wire loop 80 loosely secured thereto between washers 63 and nuts 64. The ends 80a of loop 80 are laterally outturned to engage in holes 20k and 21k provided in ankle plates 20 and 21. The bight portion 81 of the force transmitting loop 80 moves upwardly and downwardly with the movement of the plunger 60. Such bight portion is positioned in overlying engagement with the nonpivoted end portions of the latching lever 70 and is effective to rotate latching lever 70 in a counterclockwise direction whenever the plunger 60 is depressed through the application of a increased downward force to the rearmost cushion plug 50d.

The operation of the artificial foot embodying this invention should clear to those skilled in the art from the foregoing description. Briefly, the artificial foot 10 is longitudinally adjusted to fit the patient's shoe in the manner heretofore described by selecting an appropriate pair of adjustment recesses 20b and 21b in the ankle plates 20 and 21 for receiving the transverse ends 24a and 24b of the instep plate support rod 24.

With the patient's shoe applied to the artificial foot, and starting from rest position illustrated in FIG. 1, assume that the other leg is first moved forward in a step. This results in the artificial foot assuming the position illustrated in FIG. 2 wherein nuts 61 engage the bottom of plate 30 to elevate the heel portion of foot 10. The toe simulator portion 14 is pivoted upwardly or counterclockwise with respect to the sole plate 11 against the bias of the spring 16. Since the depending plunger 60 is in an elevated position, the latching lever 70 frictionally engages the control rod 15 to maintain the toe simulator 14 in the upturned position illustrated in FIG. 2. As the artificial foot is then moved forward in the course of performing its step, the toe simulator portion 14 remains in the upturned position shown in FIG. 2 and eliminates the posibility of dragging of the shoe toe during this portion of the step.

As the heel of the shoe 1 containing the artificial foot 10 strikes the walking surface at the end of the step by the artificial foot, the increased compressive force on the rear cushion plug 50d due to the pivotal movement of the prosthetic bottom plate 40 relative to the leg force receiving plate 30 causes a downward depression of the plunger 60, and this in turn causes a counterclockwise rotation of the latching lever 70 to release the control linkage 15 to permit the toe simulator 14 to return to the position shown in FIG. 1.

Thus the operation of the artificial foot corresponds very closely to that of a natural foot. In the event that the walking has to be accomplished on an uneven surface, the multi-plane cushioned pivotal movement of the prosthetic bottom plate 40 relative to the leg force receiving plate 30 provided by the plurality of spaced cushion plugs 50a, 50b, 50c and 50d permits the artificial foot to accomodate such uneven terrain in much the same manner as a natural ankle.

Modifications of this invention will be readily apparent to those skilled in the art and it is intended that the scope of the invention be determined solely by the appended claims.

What is claimed is:

1. An artificial foot adapted for insertion in a conventional shoe comprising, in combination: a sole plate insertable in the bottom portions of a shoe, a toe simulator element having its rear portion horizontally pivoted to said bottom plate, upstanding means secured to said sole plate for simulating the ankle portions of a foot, a leg force receiving plate secured to the top portions of said upstanding means, a prosthesis attachable to the leg stump and having a bottom plate disposed in generally parallel, overlying relation to said leg force receiving plate, resilient cushion means interconnecting said plates but permitting limited pivotal movement of said prosthesis plate relative to said leg force receiving plate as a consequence of walking movement of the leg stump, a spring-pressed linkage operable between said sole plate and said toe simulator to resiliently urge said toe simulator to a generally aligned position relative to said sole plate, latching means normally securing said linkage against movement, and means responsive to the pivotal movement of said prosthesis plate relative to said leg force receiving plate as the shoe strikes the ground in the step for initially releasing said latching means to permit pivotal movement of said toe simulator to said aligned position and subsequently latching said linkage in an upward position of said toe simulator as the step progresses.

2. An artificial foot adapted for insertion in a conventional shoe comprising in combination: a channel shaped sole plate insertable in the bottom portions of a shoe and having laterally spaced upstanding wall portions, a toe simulator element having its rear portion horizontally pivoted to said bottom plate side walls, upstanding plate means for simulating the ankle portions of a foot, means on said upstanding plate means for contacting the inner heel portions of the shoe, longitudinally adjustable means for connecting said upstanding plate means to said sole plate, thereby permitting length adjustment of the artificial foot, a leg force receiving plate secured to the top portions of said upstanding plate means, a prosthesis attachable to the leg stump and having a bottom plate disposed in generally parallel, overlying relation to said leg force receiving plate, resilient cushion means interconnecting said plates but permitting limited pivotal movement of said prosthesis plate relative to said leg force receiving plate as a consequence of walking movement of the leg stump, a spring-pressed linkage operable between said sole plate and said toe simulator to resiliently urge said toe simulator to a generally aligned position relative to said sole plate, latching means normally securing said linkage against movement, and means responsive to the pivotal movement of said prosthesis plate relative to said leg force receiving plate as the shoe strikes the ground in a step for initially releasing said latching means to permit pivotal movement of said toe simulator to said aligned position and subsequently latching said linkage in an upward position of said toe simulator as the step progresses.

3. An artificial foot adapted for insertion in a conventional shoe comprising in combination: a channel shaped sole plate insertable in the bottom portions of a shoe and having laterally spaced upstanding wall portions, a generally U-shaped toe simulator having its rear portion horizontally pivoted to said upstanding wall portions, a pair of laterally spaced, vertical side plates rigidly interconnected at their rear by a transverse plate portion, means on said transverse plate portion for contacting the inner heel portions of the shoe, longitudinally adjustable means for connecting said side plates to said sole plate, thereby permitting length adjustment of the artificial foot, a leg force receiving plate secured to the top portions of said side plates, a prosthesis attachable to the leg stump and having a bottom plate disposed in generally parallel, overlying relation to said leg force receiving plate, resilient cushion means interconnecting said plates but permitting limited pivotal movement of said prosthesis plate relative to said leg force receiving plate as a consequence of walking movement of the leg stump, a spring-pressed linkage operable between said sole plate and said toe simulator to resiliently urge said toe simulator to a generally aligned position relative to said sole plate, latching means normally securing said linkage against movement, and means responsive to the pivotal movement of said prosthesis plate relative to said leg force receiving plate as the shoe strikes the ground in a step for initially releasing said latching means to permit pivotal movement of said toe simulator to said aligned position and subsequently latching said linkage in an upward position of said toe simulator as the step progresses.

4. An artificial foot adapted for insertion in a conventional shoe comprising in combination: a channel shaped sole plate insertable in the bottom portions of a shoe and having laterally spaced upstanding wall portions, a generally U-shaped toe simulator having its rear portion horizontally pivoted to said upstanding wall portions, a pair of laterally spaced, vertical side plates rigidly interconnected at their rear by a transverse plate portion, means on said transverse plate portion for contacting the inner heel portions of the shoe, longitudinally adjustable means for connecting said side plates to said sole plate, thereby permitting length adjustment of the artificial foot, a transversely curved plate simulating the instep surface of the foot, means for supporting said instep plate in overlying relation to said sole plate, a leg force receiving plate secured to the top portions of said side plates, a prosthesis attachable to the leg stump and having a bottom plate disposed in generally parallel, overlying relation to said leg force receiving plate, resilient cushion means interconnecting said plates but permitting limited pivotal movement of said prosthesis plate relative to said leg force receiving plate as a consequence of walking movement of the leg stump, a spring-pressed linkage operable between said sole plate and said toe simulator to resiliently urge said toe simulator to a generally aligned position relative to said sole plate, latching means normally securing said linkage against movement, and means responsive to the pivotal movement of said prosthesis plate relative to said leg force receiving plate as the shoe strikes the ground in a step for initially releasing said latching means to permit pivotal movement of said toe simulator to said aligned position and subsequently latching said linkage in an upward position of said toe simulator as the step progresses.

5. An artificial foot in accordance with claim 1, 2, 3 or 4 wherein said latching means comprises a lever pivoted at one end to said sole plate and having a slot frictionally traversed by said linkage means, whereby the application of a downward force to the non-pivoted end of said lever frees the frictional bind on said linkage means, and said means responsive to the pivotal movement of said prosthesis plate comprises an elastomeric mass disposed between said prosthesis plate and said leg force transmitting plate and a plunger dependingly secured in said elastomeric mass and freely traversing said leg force transmitting plate to contact the non-pivoted end of said lever.

6. An artificial foot in accordance with claim 1, 2, 3 or 4 wherein said latching means comprises a lever pivoted at one end to said sole plate and having a slot frictionally traversed by said linkage means, whereby the application of a downward force to the non-pivoted end of said lever frees the frictional bind on said linkage means, and said means responsive to the pivotal movement of said prosthesis plate comprises an elastomeric mass disposed between said prosthesis plate and said leg force transmitting plate, a plunger dependingly secured in said elastomeric mass and freely traversing said leg force transmitting plate to contact the non-pivoted end of said lever, and a stop member adjustably secured to said depending plunger to pickup the rear portion of said leg force transmitting plate during the portion of the step wherein the heel portion of the artificial foot must be elevated.

7. An artificial foot in accordance with claim 3 where said longitudinally adjustable means comprises opposed longitudinaly slots in each of the bottom portions of said side wall, the bottom edge of each said slot having a plurality of longitudinally spaced vertical recesses therein, a pair of transversely aligned holes respectively provided in said upstanding wall portions, opposed pairs of said recesses being selectively alignable with said holes as said side plates are longitudinally adjusted relative to said sole plate, and rod means transversing said holes and a selected opposed pair of recesses, thereby adjusting the effective length of said artificial foot.

8. An artificial foot in accordance with claim 7 wherein said rod means comprises a U-shaped rod having each free end portion laterally outturned to respectively traverse a selected recess and one of said holes, and a transversely curved plate simulating the instep surface of a foot, said plate being supported in part in overlying relationship to said sole plate by the bight portion of said U-shaped rod, whereby the vertical position of said transversely curved instep plate varies directly with the effective length of the artificial foot.

9. An artificial foot in accordance with claim 1, 2, 3 or 4 wherein said resilient cushion means comprises at least four equi-spaced elastomeric blocks secured between said prosthesis plate and said leg force receiving plate, thereby permitting limited relative pivotal movement of said plates about a plurality of horizontal axes.

10. An artificial foot adapted for insertion in a conventional shoe comprising, in combination: a sole plate insertable in the bottom portions of a shoe, upstanding means secured to said sole plate for simulating the ankle portions of a foot, means for attaching said ankle simulating means to a prosthesis attachable to the leg stump, an instep simulating member, linkage means for positioning said instep simulating member in a plurality of vertical positions relative to said sole plate, means for longitudinally varying the point of securement of said ankle simulating means to said sole plate to change the effective length of the artificial foot, and means responsive to said last mentioned means for varying the vertical position of said instep simulating means in direct proportion to the effective length of the artificial foot.

11. An artificial foot adapted for insertion in a conventional shoe comprising, in combination: a sole plate insertable in the bottom portions of a shoe, upstanding means secured to said sole plate for simulating the ankle portions of a foot, a leg force receiving plate secured to the top portions of said upstanding means, an instep simulating member, a first linkage interconnecting said instep simulating member and said ankle simulating means, a second linkage interconnecting said instep simulating member and said sole plate, and means for longitudinally adjusting the point of securement of said ankle simulating means and said sole plate to change the length of the artificial foot and concurrently raise the position of the instep simulating member.

12. An artificial foot in accordance with claim 10 or 11 wherein said means for longitudinally adjusting the point of securement of said ankle simulating means and said sole plate comprises a horizontal hole in one of said sole plate and said ankle simulating means and a plurality of longitudinally spaced recesses in the other of said sole plate and said ankle simulating means, a pin traversing said hole and a selected one of said recesses to longitudinally fix said ankle simulating means relative to said sole plate, and means connecting said pin to said instep simulating means.

13. An artificial foot in accordance with claim 10 or 11 wherein said sole plate as a channel shaped configuration including a pair of laterally spaced side walls and said ankle simulating means comprises a pair of laterally spaced upstanding plate slidable in the channel defined by said sole plate, a transverse hole extending through both side walls of said sole plate, thereof transversely aligned longitudinally extending slots respectively provided in the bottom portions of said ankle plates and alignable with said transverse holes, a plurality of longitudinally spaced vertical recesses along the bottom edge of each of said longitudinal slots, a generally U-shaped rod having the free end portions thereof laterally outturned and respectively engagable with a selected one of said recesses and the adjacent hole in said sole plate side walls, and means for pivotally securing the bight portion of said U-shaped rod to said instep simulating means.

* * * * *